United States Patent [19]

Deibig et al.

[11] 4,451,452
[45] May 29, 1984

[54] PHARMACEUTICAL COMPOSITIONS CONTAINING BIODEGRADABLE POLYMERS

[75] Inventors: Heinrich Deibig, Frankfurt; Roland Reiner, Eschborn, both of Fed. Rep. of Germany; Hendricus B. A. Welle, Maarssen, Netherlands

[73] Assignee: Sandoz Ltd., Basel, Switzerland

[21] Appl. No.: 323,733

[22] Filed: Nov. 23, 1981

[30] Foreign Application Priority Data

Nov. 29, 1980 [DE] Fed. Rep. of Germany ....... 3045135

[51] Int. Cl.$^3$ ...................... A61K 31/74; A61K 31/78
[52] U.S. Cl. ........................................ 424/78; 424/81; 424/250; 424/261; 424/361
[58] Field of Search ............................ 424/78, 81, 361

[56] References Cited

U.S. PATENT DOCUMENTS

| | | |
|---|---|---|
| 3,081,233 | 3/1963 | Enz et al. |
| 3,499,962 | 3/1970 | Wurzburg et al. |
| 3,773,919 | 11/1973 | Boswell et al. ............... 424/19 |
| 3,978,203 | 8/1976 | Wise ............................ 424/22 |
| 4,209,513 | 6/1980 | Torode et al. ............... 424/228 |

FOREIGN PATENT DOCUMENTS

| | | |
|---|---|---|
| 751427 | 1/1953 | Fed. Rep. of Germany. |
| 810306 | 3/1959 | United Kingdom. |
| 902369 | 8/1962 | United Kingdom. |

OTHER PUBLICATIONS

Merck Index, 9th ed., 1976, pp. 386, 387 & 986, para. 2904 & 7363.
Webster's Seventh New Collegiate Dictionary, p. 31, 1967.
Chemical Abstracts 79:79306s, (1973).
Chemical Abstracts 81:170012v, (1974).
"Kexikon der Hilfsmittel", Fiedler, 2nd Edn., 1981.

*Primary Examiner*—Leonard Schenkman
*Attorney, Agent, or Firm*—Gerald D. Sharkin; Robert S. Honor; Walter F. Jewell

[57] ABSTRACT

Polymers formed by incomplete esterification of the hydroxy groups of a water-soluble polymer such as polyvinyl alcohol, amylose or dextran with a pharmacologically acceptable mono- or di-carboxylic acid to an extent sufficient to render the polymer water-insoluble although still water-swellable, are biodegradable. They are useful for the formulation of pharmaceutical compositions for parenteral administration, particularly in the form of injectable fine particles in which a drug is intimately mixed with or encapsulated by the polymer.

8 Claims, No Drawings

PHARMACEUTICAL COMPOSITIONS CONTAINING BIODEGRADABLE POLYMERS

This invention relates to pharmaceutical retard compositions comprising a drug and a biodegradable polymer.

It is known from U.S. Pat. No. 3 773 919 to make compositions of this type using polylactic acid as the biodegradable polymer. It has also been proposed in U.S. Pat. No. 3,978,203 to use biodegradable polymers based on the condensation of a physiologically acceptable polyol such as glycerol with a poly-carboxylic acid which occurs in the metabolic Krebs cycle, so as to form a cross-linked or linear polyester.

According to the present invention the biodegradable polymer may be obtained by acylation of a pharmacologically acceptable water-soluble polymeric hydroxy compound with a fatty acid derivative, the product containing sufficient ester groups to be lipophilic in nature. Such a polymer is gradually hydrolysed by tissue fluids until sufficient ester groups have been lost for the polymer to become hydrophilic and finally water-soluble. At this stage the hydrolysed polymer dissolves in the tissue fluids and is excreted by the kidneys.

A suitable choice of the polymeric hydroxy compound, the acylating groups and the degree of acylation enables a wide range of polymers of different properties and hydrolysis rates to be prepared.

The present invention therefore provides pharmaceutical compositions comprising a pharmacologically active material in intimate mixture with, or wholly or partly encapsulated by, a biodegradable polymer which is based upon a pharmacologically acceptable water-soluble polymer having hydroxy groups attached to the polymer chain, less than all of said hydroxy groups being esterified by residues of pharmacologically acceptable mono- or di-carboxylic acids, the degree of esterification being such that the biodegradable polymer is water-swellable but water-insoluble under physiological conditions.

Pharmacologically acceptable water-soluble hydroxy polymers are those which are of low toxicity and antigenicity, and which are themselves excretable or which are metabolised to excretable derivatives. Suitable polymers include polymers which have found use as plasma expanders, for example poly(vinyl alcohol) (PVA), and dextran; and soluble starch products for example amylose and hydroxyethyl starch. Other suitable materials include hydroxy-containing acrylic polymers, for example hydroxyethyl methacrylate. In order for such polymers to be directly excretable, their molecular weight should not be greater than 50,000–60,000, but polymers of molecular weight up to 200,000 may be used if they can be enzymatically degraded to fractions of lower molecular weight.

Pharmacologically acceptable mono- or di-carboxylic acids, whose residues are suitable for esterification of the hydroxy polymer, are those of low toxicity which are readily metabolised and/or excreted. Preferably they are acids which occur in normal metabolism, for example straight-chain fatty acids. Preferred residues of straight-chain fatty acids are those having from 1 to 10, preferably 1 to 6, carbon atoms. More preferred acid residues are formyl and those having an even number of carbon atoms, particularly acetyl and butanoyl.

Suitable residues of di-carboxylic acids are for example residues of succinic, maleic, fumaric and malonic acid, particularly succinic acid. Esters containing residues of di-carboxylic acids will have free carboxylic acid groups, which may be in free acid or in salt form or which may be further chemically modified, or which may react chemically with the active material, for example to form a salt.

The degree of acylation of the hydroxy polymer (defined as the percentage of available hydroxy groups which are acylated) must be sufficient to render the polymer lipophilic and water-insoluble, but should not be so high that the polymer will not be penetrable or swellable by water. In general, the degree of acylation is suitably at least 30%, preferably at least 50%, more preferably at least 65%. The upper limit of the degree of acylation is 98%, preferably 95%, more preferably 90%. As the degree of acylation of a given polymer system is increased, the polymer becomes progressively less water-soluble and more slowly hydrolysable by tissue fluids. If for a given hydroxy polymer the acylating group is changed, it is found that the larger the acylating group, the lower degree of acylation is required to obtain the same solubility and hydrolysis properties.

It is of course possible to employ a mixture of different acylating groups with the same hydroxy polymer. In particular a polymer partially esterified with residues of a straight-chain fatty acid may be further esterified with residues of a di-carboxylic acid; for example a partially acetylated PVA may be further esterified with succinic acid residues.

The biodegradable polymers used in the compositions of the present invention may be prepared in conventional manner by the reaction of the hydroxy polymer with an acylating agent, for example an acid anhydride or acid chloride, or with the corresponding acid itself. Although the biodegradable polymers are described herein as acylation products of hydroxy polymers, it will be appreciated that this is a description of the chemical structure of the polymers and is not to be taken as excluding polymers of this structure prepared by different routes. Thus it may be convenient in some cases to begin with a fully acylated polymer, for example poly(vinyl acetate), obtained commercially by the polymerisation of vinyl acetate monomer, and carry out a partial hydrolysis of the ester groups.

Pharmaceutical compositions according to the invention may contain any pharmacologically active material which it is desirable to administer in retard form over a period of days or weeks. Such active materials may for example include such drugs as narcotic antagonists, for example naloxone; antipsychotic agents, for example chlorpromazine; analgetics; steroidal and non-steroidal fertility control agents; anti-asthmatics, e.g. ketotifen; $\beta$-receptor blockers; coronary vasodilators; natural and synthetic hormones, for example calcitonin and somatostatin; ergot alkaloid derivatives, for example dihydroergotamine, dihydroergotoxin and bromocriptine; and anticoagulants, for example heparin. Particularly suitable are drugs which normally must be administered at relatively frequent intervals over a considerable period, particularly where the unit dosage is small and especially where parenteral administration is required.

The compositions of the invention may be administered in the form of shaped articles for implantation either subcutaneously or in a body cavity; or, preferably, in a form suitable for subcutaneous or intramuscular injection. Shaped articles may for example be in the form of films or tablets, or may be in the form of cylinders of 1–2 mm diameter which can be introduced subcutaneously with a wide-bore needle. They may also be part of a prosthetic device which is in contact with tissue fluids. Injectable preparations are most suitably in the form of small particles, for example of up to 100 μm diameter, which are suspended in a suitable carrier, for example sterile saline solution or vegetable oil.

The drug may be either intimately mixed with the biodegradable polymer, or wholly or partially encapsulated therewith, and the corresponding compositions may be prepared in accordance with known techniques. Thus intimate mixing may be achieved by dissolving the drug and the polymer in a common solvent which is then evaporated. If the polymer is film-forming, the residual material may be in the form of a cast film; alternatively the material may be consolidated by being pressed into a shaped form such as a tablet, preferably at a temperature above the softening point of the polymer, but below that at which the drug is adversely affected. If the drug is sufficiently heat-stable it may be possible to obtain intimate mixing by dissolving or dispersing the drug in a melt of the polymer, with subsequent cooling.

In order to produce fine particles of intimately mixed drug and polymer, a solid article produced as described above may be finely ground, for example by milling, and the particles sieved to isolate the required size range. Alternatively a common solution of drug and polymer may be subjected to spray drying, or a solution of drug in a polymer melt may be spray-frozen. The fine particles may be kept from coagulation by suspending them in a protective colloid, for example a dilute aqueous solution of PVA having a molecular weight of less than 50,000.

In order to produce a shaped article comprising a drug encapsulated by polymer, a tablet or pellet of drug may be coated with polymer from a melt or solution. Small particles (microcapsules) of drug wholly or partially encapsulated by polymer may be obtained by any of several known techniques for microencapsulation, for example spray drying of a suspension of small drug particles in a solution of the polymer, coacervation processes in which polymer is deposited from solution upon suspended drug particles, and emulsion processes in which a suspension of drug particles in a solution of polymer is emulsified in an aqueous medium and the non-aqueous solvent evaporated.

It is preferred that the composition be an intimate mixture comprising a solid solution or dispersion of drug in a matrix of polymer, or be in microencapsulated form. Macroscopic articles comprising a drug coated with a layer of polymer, e.g. coated tablets, are less preferred.

The suitability of a pharmaceutical composition according to the invention for use as a long-term drug delivery system may be evaluated by study of the rate of dissolution of the polymer and the rate of release of drug from the composition.

Preliminary studies can be made in vitro, the weight loss of a pellet of the pure polymer (without drug) being measured after exposure to physiological saline or calf serum for periods of 1 month or more, or the rate of release of drug into a saline or serum medium being measured for a composition containing both drug and polymer. In vivo tests require the injection or implantation of polymer or polymer/drug composition into test animals, for example rats; the use of radioactive labelled drug enables the rate of drug release to be monitored, whereas the disappearance of polymer may be determined histologically.

Ideally for long-term administration, the release of drug should follow zero-order kinetics; i.e. the rate of release should be constant over a period (the "release time") at the end of which substantially all the drug has been released. The polymer should ideally persist intact for the entire release time, and should disappear completely whithin a period approximately 3 times as long as the release time. Thus for example if a composition according to the invention is administered at monthly intervals and the release time is one month, a constant rate of release of drug will be achieved while the amount of polymer present in the body at any time will not exceed 3 times the monthly dosage. Alternatively, it may for some applications be desirable to have an initial rapid rate of drug release, followed by a slower release rate, corresponding approximately to first order kinetics.

The release time and the disappearance time will of course depend upon the polymer and drug chosen, the degree of acylation of the polymer, the method of preparation of the composition and the particle size and surface/volume ratio of the composition. It is an advantage of the present invention that the results desired for the administration of a given drug may be obtained by a suitable variation of the above parameters, such variation being within the skill of the man in the art.

Particularly preferred biodegradable polymers are amylose acetate, PVA formate, amylose butyrate and dextran butyrate having degrees of acylation between 50% and 95%. Particularly preferred compositions are compositions comprising these polymers together with dihydroergotoxin, bromocriptin, ketotifen, calcitonin or somatostatin, especially compositions of dextran butyrate and amylose butyrate with ketotifen.

The following Examples illustrate the invention:

EXAMPLES 1–10: Preparation of polymers

Example 1: PVA Formate 10 g PVA of molecular weight approx. 25,000 (Polyviol M 05/20, Wacker) is dissolved in 200 ml 95% formic acid and left to stand 5 days at room temperature. The product is precipitated with absolute methanol, filtered, washed with methanol and dried to constant weight, giving 12.7 g of a product determined by hydrolysis and titration to have a degree of acylation of 83%.

By changing the concentration of formic acid between 80 and 100%, PVA formate having a degree of acylation between 63% and 98% may be obtained.

Example 2: PVA Acetate 43 g poly(vinyl acetate) having a MW of approx. 36,000 is dissolved in 172 g t-butanol at 80° C., 4.2 g potassium hydroxide (in 30% aqueous solution) is added dropwise with stirring, and the mixture is refluxed for 5 hours. The product is precipitated with water, filtered, washed with water and dried to constant weight, giving 25.5 g of polymer having a degree of acylation of 85%.

By changing the reaction time and the quantity of alkali used, products with degrees of acylation from 45% to 89% may be obtained.

Example 3: PVA Butyrate 5 g Polyviol M 05/20 is dissolved by warming in a mixture of 75 ml formamide and 75 ml pyridine under a nitrogen atmosphere. After cooling 49 g butyric anhydride (mol ratio vinyl alcohol : butyric anhydride = 1:1.5) is added and the mixture left at room temperature for 24 hours. The reaction mixture is then dispersed with vigorous stirring in an equal volume of water, whereupon an aqueous phase and an oily phase separate. The oily phase is separated, taken up in 200 ml methanol and slowly added with stirring to 1.2 l water. The product is filtered, washed with water and dried to constant weight, giving 7.1 g of polymer having a degree of acylation of 49%.

By varying the quantity of butyric anhydride and the reaction time, polymers with degrees of acylation from 29% to 84% may be obtained.

Example 4: Dextran acetate 5 g Dextran is dissolved in 75 ml formamide and treated with 75 ml pyridine. The reaction mixture is cooled to −10° C. and 65 ml acetic anhydride added dropwise over 60 minutes. The mixture is stirred for 24 hours at −10° C. under nitrogen, then poured into ice water. The product is filtered, washed with water and dried to constant weight, giving 7.0 g of a polymer of degree of acylation 90%.

Example 5: Dextran butyrate

In analogy to Example 4, but operating at −20° C. and using 120 g butyric anhydride, dextran butyrate (7.0 g) having a degree of acylation of 63% is obtained. By varying the quantity of butyric anhydride and/or the reaction time, a degree of acylation of 34–86% can be obtained.

Example 6: Amylose acetate

In analogy to Example 4, using amylose in place of dextran, amylose acetate having a degree of acylation of 80% is obtainted.

Example 7: Amylose butyrate

In analogy to Example 4, using amylose in place of dextran and using butyric anhydride in place of acetic anhydride, amylose butyrate having a degree of acylation of 43–82% is obtained, depending on the reaction time and the quantity of butyric anhydride.

Example 8: Amylose acetate hemi-succinate 2 g of the amylose acetate of Example 6 is dissolved in 50 ml formamide+ml pyridine at room temperature, and 0.47 g succinic anhydride is added. The mixture is left for 5 days at room temperature, and then precipitated with water. The product is filtered, washed with water, dilute HCl and again water, and dried to constant weight. 1.15 g of succinylated amylose acetate is obtained.

Example 9: Dextran acetate butyrate

Example 4 is repeated, using in place of acetic anhydride a mixture of 30 g acetic anhydride and 60 g butyric anhydride, to give dextran acetate butyrate.

Example 10: Hydroxyethyl starch butyrate

Example 3 is repeated using hydroxyethyl starch in place of polyvinyl alcohol. Hydroxyethyl starch butyrate is obtained.

The polymers of Examples 1 to 8 were tested for their fabricability into pellets by hot pressing at 120°–200° C., using a Teflon film to prevent sticking. Pellets of 9.8 mm diameter and 1.5 mm thickness were prepared. The effect of physiological saline at 37° C. on the pellets was tested, swellability under physiological conditions being indicated by the weight of water taken up after immersion for 65 hours. The results are shown in Table I.

TABLE I

| Example No. | Polymer | Degree of acylation (%) | Press temp. °C. | Appearance of pellet | Water uptake in 65 hours (%) |
|---|---|---|---|---|---|
| 1 | PVA formate | 83 | 120 | clear, ductile | 6.9 |
| 2 | PVA acetate | 85 | 120 | cloudy, brittle | (disintegrated) |
| 3 | PVA butyrate | 49 | 120 | cloudy, elastic | 6.9 |
| 4 | dextran acetate | 90 | 200 | (remained as powder) | — |
| 5a | dextran butyrate | 34 | 150 | cloudy, brittle | (disintegrated) |
| 5b | dextran butyrate | 51 | 120 | clear, brittle | 12 |
| 5c | dextran butyrate | 63 | 120 | clear, brittle | 5.6 |
| 5d | dextran butyrate | 81 | 120 | clear, brittle | 1.9 |
| 6 | amylose acetate | 79 | 200 | clear, brittle | 8.9 |
| 7 | amylose butyrate | 63 | 120 | clear, brittle | 2.6 |
| 8 | succinylated amylose acetate | — | 120 | clear, brittle | 9.5 |

Because in this test the polymer is in the form of a large pressed tablet, the polymer may be regarded as water-swellable if it takes up any appreciable quantity of water. The amount of water taken up would of course be much greater if the polymer were in finely divided form. Polymers which dissolve under the conditions of this test are not suitable for use in pharmaceutical compositions according to the invention.

EXAMPLES 11–16: Preparation of shaped solid compositions

Example 11

10 g of the PVA formate of Example 1 is dissolved in chloroform and a solution of 2.5 g (−)allyl-9,9-dimethyl-2′-hydroxy-6,7-benzomorphan (ADHB) hydrochloride salt in chloroform is added. The mixed solution is evaporated to dryness in a rotary evaporator at 40° C. under vacuum. The residue is pressed into pellets at 120° C. as described for the polymer alone, giving cloudy, brittle pellets.

Example 12

10 g of PVA having a degree of acylation of 98% is swollen into a gel by the addition of chloroform. A solution of 2.5 g of the maleate salt of the benzoyl ester of ADHB in chloroform is added and left in contact with the gel for 3 days at room temperature. The mixture is evaporated, dried and pressed into pellets as in Example 11.

Example 13

10 g of the dextran butyrate of Example 5 is dissolved in chloroform and a suspension of 2.5 g ADHB pamoate salt in chloroform is added. The mixture is evaporated, dried and pressed into pellets as in Example 11.

Example 14

10 g of PVA formate having a degree of acylation of 98% is mixed with 2.5 g of ADHB pamoate and the solids are cooled to dry ice temperature ($-80°$ C.) and ground together. The mixed powder is pressed into pellets at 120° C.

Example 15

A composition comprising 80% by wt. of dextran butyrate having a degree of acylation of 53% and 20% by wt. of the free base form of ADHB is prepared by the method of Example 11.

Example 16

A composition comprising 80% by wt. of amylose acetate having a degree of acylation of 70% and 20% by wt. of ADHB benzoyl ester maleate is prepared by the method of Example 11.

Examples 17–22: Preparation of particle suspensions

The polymer/drug evaporated residues or mixed powders prepared according to Examples 11–16 are ground finely in a mortar under liquid nitrogen, then dried over $P_2O_5$ under vacuum, and finally sieved. The sieve fraction of 40–125 μm particle diameter is taken up in 99 ml water containing 1 g PVA (MW 20,000) and 11 ml 1-M phosphate buffer (pH 7.4).

EXAMPLES 23–29: Microencapsulation by emulsion method

Example 23

10 g of finely divided bromocryptine free base is added to a solution of 10 g of dextran butyrate having a degree of acylation of 42% (DB 42) in 100 ml of methylene chloride. This organic phase is poured into an aqueous solution of 1% (wt.) gelatine at 21° C. buffered to pH 6.9 and stirred vigorously for 1 hour, during which time the methylene chloride evaporates. The resulting microcapsules are collected by filtration, washed with water and dried. In vitro tests showed a moderate rate of drug release.

EXAMPLES 24–29

Example 23 was repeated using either bromocryptine free base (B) or ketotifen free base (K) as pharmacologically active material, and using either DB 42, dextran butyrate 86% acylated (DB 86) or amylose butyrate 82% acylated (AB 82) as polymer. The quantities of drug, polymer and solvent, the pH of the aqueous phase and the type of in vitro drug release are shown in Table II. The microcapsules had diameters in the range 5–90 μm.

Table II

| Example No. | 24 | 25 | 26 | 27 | 28 | 29 |
|---|---|---|---|---|---|---|
| Drug used | B | B | K | K | K | K |
| weight (g) | 10 | 10 | 5 | 5 | 10 | 10 |
| polymer | DB86 | AB82 | DB86 | AB82 | DB86 | AB82 |
| weight (g) | 10 | 10 | 15 | 15 | 10 | 10 |
| Volume CH$_2$Cl$_2$ (ml) | 80 | 80 | 80 | 80 | 60 | 60 |

Table II-continued

| Example No. | 24 | 25 | 26 | 27 | 28 | 29 |
|---|---|---|---|---|---|---|
| pH of aqueous phase | 6.9 | 6.9 | 7.4 | 7.4 | 7.4 | 7.4 |
| type of release | mod. | mod. | v. slow | mod. | fast | v. fast |

EXAMPLES 30–35: Microencapsulation by spray drying

Example 30

5 g of finely divided ketotifen free base is added to a solution of 15 g DB 42 in 200 ml methylene chloride, and the suspension is sprayed into a spray drying apparatus at an air temperature of 59° C. to give microcapsules having a moderate rate of drug release in vitro.

Examples 31–35

Example 30 is repeated using different polymers and conditions as shown in Table III, with 5 g ketotifen in each case.

Table III

| Example No. | 31 | 32 | 33 | 34 | 35 |
|---|---|---|---|---|---|
| Polymer used | DB86 | AB82 | DB86 | DB86 | AB82 |
| weight (g) | 15 | 15 | 15 | 15 | 15 |
| volume CH$_2$Cl$_2$ (ml) | 150 | 150 | 400 | 200 | 400 |
| air temp. (°C.) | 68 | 57 | 57 | 62 | 68 |
| type of release | v.slow | slow | mod. | slow | mod. |

The microcapsules had diameters in the range 1–50 μm.

What is claimed is:

1. A pharmaceutical composition comprising an effective amount of a parenterally effective drug in an injectable preparation in a sterile carrier liquid which preparation is an intimate mixture of a solid solution or dispersion of drug in a matrix of a biodegradable polymer or wholly or partly microencapsulated by a biodegradable polymer, said biodegradable polymer being a pharmacologically acceptable water-soluble polymer having hydroxy groups attached to the polymer chain, in which less than all of said hydroxy groups are esterified by residues of pharmacologically acceptable mono- or di-carboxylic acids, the degree of esterification being such that said biodegradable polymer is water-swellable but water-insoluble under physiological conditions.

2. A composition according to claim 1, in which the biodegradable polymer is based on a water-soluble polymer selected from poly(vinyl alcohol), dextran, a soluble starch product or a hydroxy-containing acrylic polymer, between 30% and 98% of the free hydroxyl groups of which are esterified with residues of pharmacologically acceptable mono- or di-carboxylic acids.

3. A composition according to claim 2, in which the water-soluble polymer is esterified with residues of a $C_1$–$C_{10}$ straigh-chain fatty acid.

4. A composition according to claim 3 in which the fatty acid is formic acid or a $C_2$–$C_6$ straight chain fatty acid having an even number of carbon atoms.

5. A composition according to claim 2 in which the biodegradable polymer is amylose acetate, PVA formate, amylose butyrate or dextran butyrate.

6. A composition according to claim 5 in which the biodegradable polymer is amylose butyrate or dextran butyrate and the pharmacologically active material is ketotifen.

7. A composition according to claim 1 comprising fine particles of mean diameter less than 100 μm.

8. A composition according to claim 7 in which the particles are suspended in an aqueous solution of a protective colloid.

* * * * *